United States Patent [19]
Ota

[11] Patent Number: 5,347,329
[45] Date of Patent: Sep. 13, 1994

[54] APPARATUS FOR OPHTHALMIC TREATMENT USING A LIGHT BEAM

[75] Inventor: Yasuo Ota, Gamagori, Japan

[73] Assignee: Nidek Co., Ltd., Gamagori, Japan

[21] Appl. No.: 921,696

[22] Filed: Jul. 30, 1992

[30] Foreign Application Priority Data

Jul. 31, 1991 [JP] Japan .................... 3-215816

[51] Int. Cl.$^5$ ............................................. A61B 3/10
[52] U.S. Cl. ...................... 351/221; 606/4; 606/12; 606/13
[58] Field of Search ............... 351/211, 221; 606/4, 606/5, 6, 10, 11, 12, 13, 14, 15, 16; 607/89

[56] References Cited

U.S. PATENT DOCUMENTS

| | | | |
|---|---|---|---|
| 4,854,693 | 8/1989 | Ichihashi et al. | 606/4 |
| 4,866,243 | 9/1989 | Sakane et al. | 606/4 |
| 4,870,952 | 10/1989 | Martinez | 606/4 |
| 5,092,865 | 3/1992 | Rink | 606/10 |
| 5,098,426 | 3/1992 | Sklar | 606/4 |
| 5,104,391 | 4/1992 | Ingle et al. | 606/11 |
| 5,139,494 | 8/1992 | Freiberg | 606/16 |
| 5,154,707 | 10/1992 | Rink et al. | 606/12 |
| 5,157,750 | 10/1992 | Grace et al. | 606/10 |
| 5,226,903 | 7/1993 | Mizuno | 606/10 |
| 5,236,360 | 8/1993 | Levy | 606/16 |

OTHER PUBLICATIONS

Copy of application filed in the United States Patent and Trademark on Nov. 14, 1991 with U.S. Serial No. 07/791,692 claiming priority of Japanese Patent Application No. Hei. 2-312006.

*Primary Examiner*—Richard A. Bertsch
*Assistant Examiner*—Howard R. Richman
*Attorney, Agent, or Firm*—Finnegan, Henderson Farabow, Garrett & Dunner

[57] ABSTRACT

An apparatus for optical treatment using a light beam, which includes an apparatus body having a first control operation device for providing an optical treatment light and an optical fiber cable for introducing an optical treatment light from the apparatus body into a delivery unit. The apparatus comprises a light relaying device connected with both of the apparatus body and the delivery unit through the optical fiber cable, second control operation device provided in the light relaying device, optical communication device for transmitting and receiving light signals, the optical communication device being arranged in the apparatus body and the light relaying device respectively, an optical system for introducing the light signals which the optical communication device transmits and receives through the optical fiber cable.

15 Claims, 2 Drawing Sheets

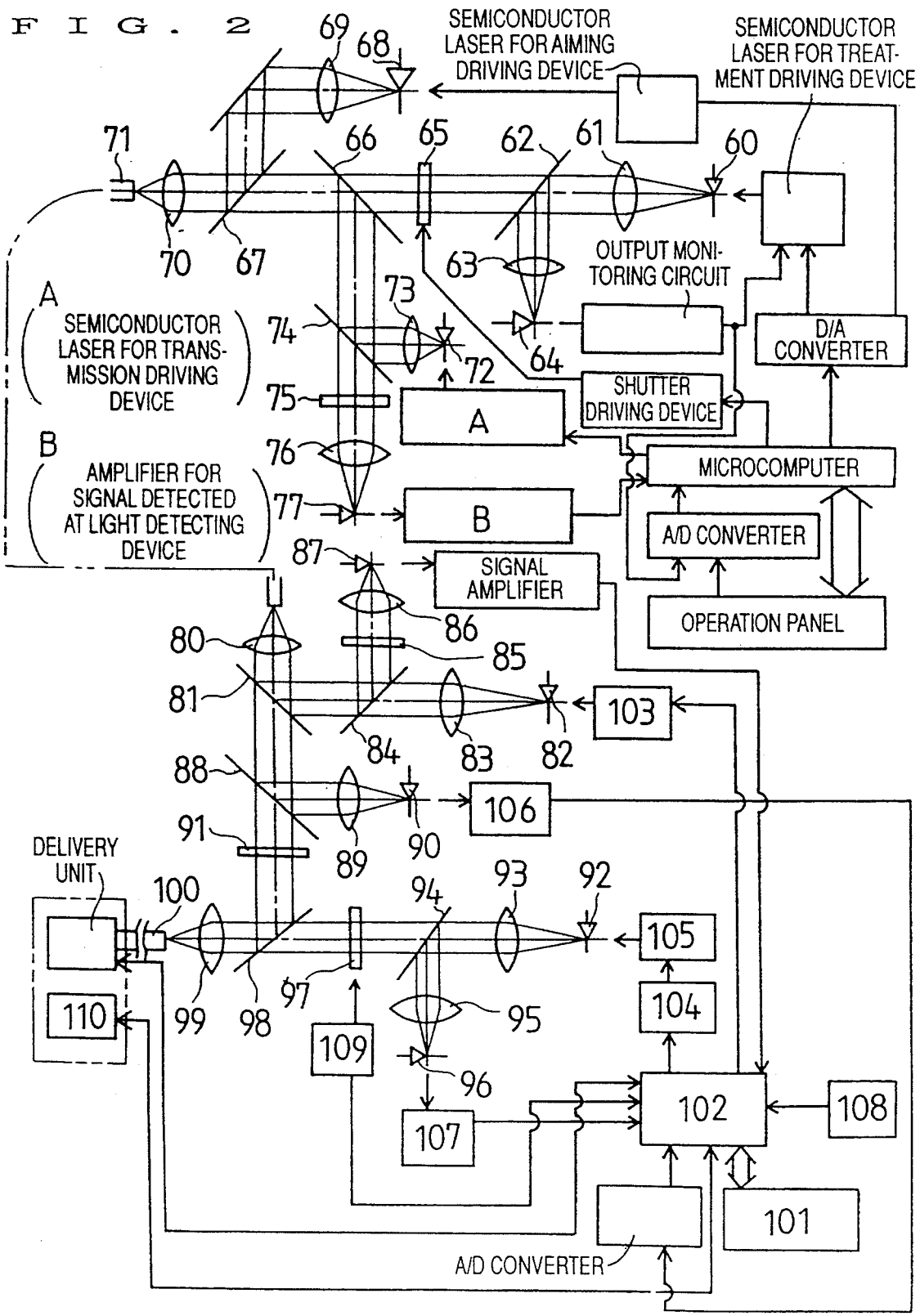

APPARATUS FOR OPHTHALMIC TREATMENT USING A LIGHT BEAM

BACKGROUND OF THE INVENTION

1. Field of the Invention

The present invention relates to an apparatus for ophthalmic treatment using photocoagulation by a light beam.

2. Description of Related Art

There is known an apparatus for optical treatment to treat a patient's eye by irradiating a laser beam into its affected part, wherein the laser beam is introduced from an apparatus body into delivery unit, for example a probe or a microscope, through an optical fiber cable.

However, because the apparatus body is large in size and provided with a cooling system, it is impossible to move it easily.

In case of the use in different places such as a treatment room, an operating room, or plural operating rooms, plural apparatuses for ophthalmic treatment are generally provided. Additionally, use is made of an apparatus having an extended optical fiber cable and a control box which is connected to a body of the apparatus by a separate communication cable pulled from the body of the apparatus.

Further, an ophthalmic apparatus is proposed in Japanese patent Application No. HEI 2-312006 (Title of the invention: Adaptor for photocoagulation) by the present applicants, in which an optical fiber cable is provided with an adaptor for photocoagulation using a laser beam to compensate an emitting power of a semiconductor laser beam, the adaptor connected with the apparatus body through a communication cable.

During an ophthalmic operation using such apparatus mentioned above, it is possible to move easily the control box and the adaptor as needed for the operation. However, when the control box and the adaptor are frequently moved, the communication cable and line get entangled with each other, thereby causing the break down of the cable.

Additionally, when connected with plural control boxes arranged in different places, the communication cable is apt to affected by an electromagnetic and electrostatic influence from its surrounding environment, thereby causing a malfunction and attenuation of the signal.

SUMMARY OF THE INVENTION

The present invention has been made in view of the above circumstances and has as an object to overcome the above problems and to provide an apparatus for optical treatment using a light beam, which apparatus reduces physical problems, such as a breaking of apparatus communication cables caused by entanglement which occurs during the movement of the apparatus control box and adaptor. The communication cable of the apparatus connects the adaptor with the apparatus body which is not affected by the electromagnetic and electrostatic influence, even if laid in different places.

Additional objects and advantages of the invention will be set forth in part in the description which follows and in part will be obvious from the description, or may be learned by practice of the invention. The objects and advantages of the invention may be realized and attained by means of the instruments and combinations particularly pointed out in the appended claims.

To achieve the objects in accordance with the purpose of the invention, as embodied and broadly described herein, an apparatus for optical treatment using a light beam, which includes an apparatus body having a first control operation means for providing an optical treatment light and an optical fiber cable introducing an optical treatment light from the apparatus body into a delivery unit, comprises a light relaying device connected with both of the apparatus body and the delivery unit through the optical fiber cable, second control operation means provided in the light relaying device, optical communication means for transmitting and receiving light signals, the optical communication means is arranged in the apparatus body and the light relaying device respectively, an optical system for introducing the light signals which the optical communication means transmits and receives through the optical fiber cable.

According to the apparatus for optical treatment of this invention, it is possible to reduce physical problems like the breaking of cables which occurs by their entanglement on the movement of the control box or the adaptor, and further to remove the electromagnetic and electrostatic influence on the communication cable even if laid in different places.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings:

FIG. 2 is a block diagram to show the arrangement of an apparatus body and an adaptor in an apparatus for optical treatment using photocoagulation embodying this invention.

DETAILED DESCRIPTION OF THE PREFERRED EMBODIMENTS

Figure 1:
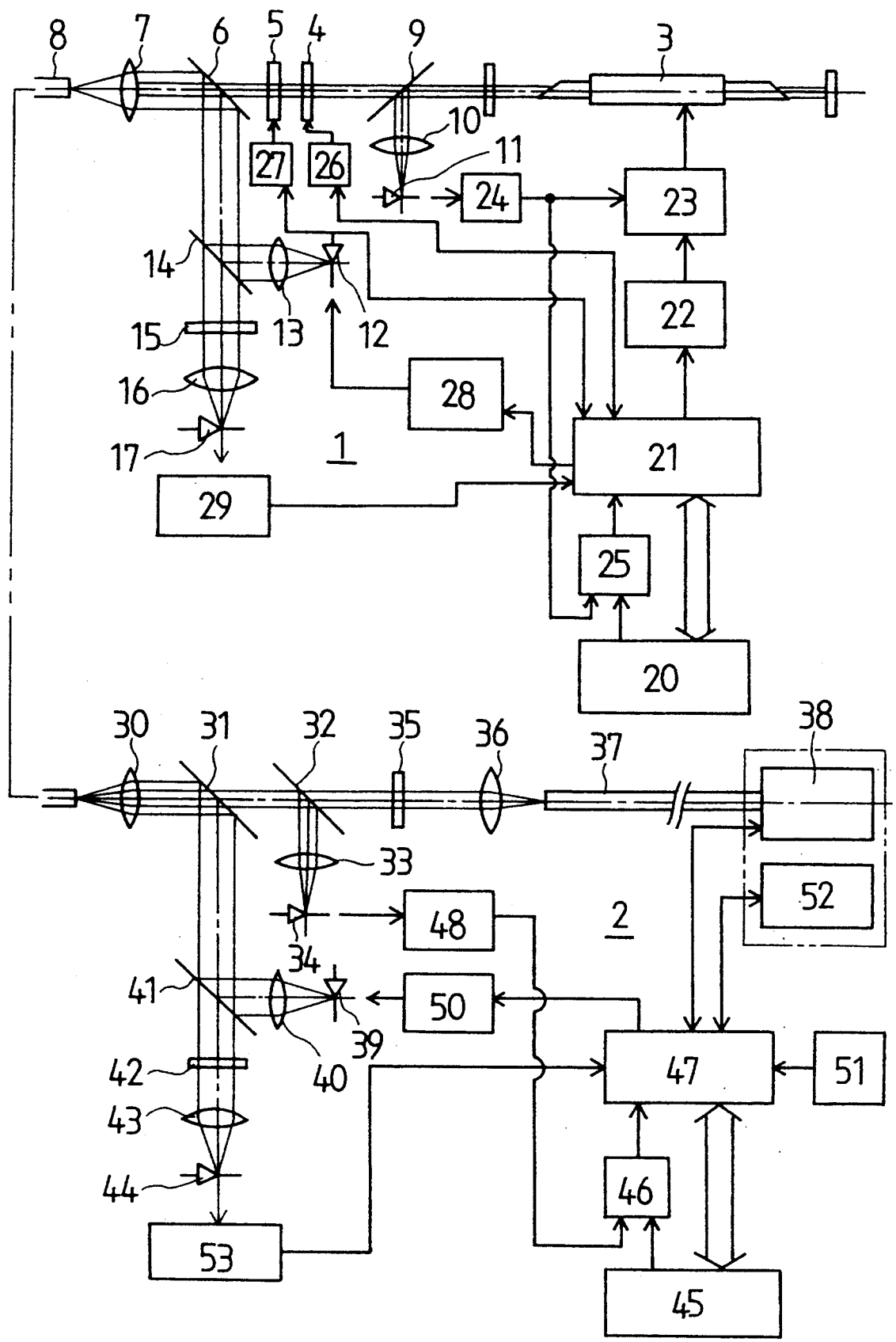
FIG. 1 is a block diagram to show the arrangement of an apparatus body and a control box in an apparatus for optical treatment using photocoagulation embodying this invention.

A detailed description of one preferred embodiment of an apparatus for optical treatment embodying the present invention will now be given referring to the accompanying drawings.

In FIG. 1, a block diagram shows an arrangement of an apparatus body 1 and a control box 2 in an apparatus for optical treatment.

Laser photocoagulation apparatus body

First, in the apparatus body for photocoagulation using a laser beam, its optical system comprises an argon laser 3 for emitting a treatment light which has the wavelength of 488 nm and 514.5 nm, a safety shutter 4 for opening or closing the optical path, an attenuator 5 for attenuating the laser beam emitted from the argon treatment laser 3 in order to use it as an aiming beam, a dichroic mirror 6 for transmitting the light which has the wavelength of 488 nm and 514.5 nm, and for reflecting the light having wavelength of 1300 nm, a condenser lens 7 for condensing the laser beam into the edge plane of an optical fiber 8, and a beam splitter 9 for reflecting a part of the laser beam emitted from the argon treatment laser 3.

The reflected light on the beam splitter 9 is incident on a light detecting device 11 after being condensed through a condenser lens 10, and its detected value is used for monitoring the emission of the laser beam.

Further, in the apparatus body, there is also provided a communication means which comprise; a semiconductor communication laser 12 for emitting a laser beam having the wavelength of 1300 nm, which is used as a light source for transmitting communication light to the control box 2, a collimating lens 13, a half mirror 14 (instead thereof, a polarizer may be used), a band pass filter 15 for transmitting communication light which has the wavelength of 1300 nm transmitted through the optical fiber 8 from the control box 2, a condenser lens 16 for condensing the transmitted communication light from the control box 2 into the light detecting device 17.

Next, in the control system of the apparatus body, an operation device 20 is provided with a setting switch for setting a treatment condition, such as the laser beam emitting condition, and a safety switch. The signal of the operation device 20 is inputted into a microcomputer 21. An output signal of the microcomputer 21 is sent to a laser driving device 23 through a D/A converter 22 to control the argon treatment laser 3.

The emitting power of the argon treatment laser 3 is monitored at the emitting monitor circuit 24 through the light detecting device 11. Then, its monitored signal is adjusted by compared with an instructed emitting power at the laser driving device 23, while transmitted into a microcomputer 21 through A/D converter 25 to monitor for abnormal emission of the argon treatment laser 3. If abnormal emission is detected, the microcomputer 21 controls the safety shutter 4 through the shutter driving device 26 and the attenuator 5 through the filter drive device 27.

In a communication means, a transmitting laser driving device 28 controls the emission of the semiconductor communication laser 12, and a receiving circuit 29 reads signals transmitted light communication through the optical fiber 8 from the control box 2 by processing the results detected at the detecting device 17.

Control Box

In the optical system of the control box 2 as a light relaying device, the emitted light from the optical fiber 8 is formed into the parallel luminous flux through a collimating lens 30. While transmitting the light which has the wavelength of 488 nm and 514.5 nm as the treatment light for a patient, a dichroic mirror 31 reflects the light of 1300 nm as the communication light received from the optical fiber 8.

A part of the received treatment light is reflected on a beam splitter 32, and the amount of the reflected light is detected at a detecting device 34 through a condenser lens 33, thereby the laser emitting power from the optical fiber 8 is detected. As a result, an abnormal emission of the optical fiber 8 is detected.

Further, the treatment light transmitted through the beam splitter 32 is condensed into the edge plane of another optical fiber 37 by a condenser lens 36 through a filter 35, and the condensed laser beam is introduced into a unit 38 through the optical fiber 37 for delivery to a patient. The filter 35 cuts any light having the wavelength of 1300 nm so as to prevent communication light from being incident to the delivery unit 38.

Communication means in the control box 2 includes semiconductor communication laser 39 that emits a communications transmission laser beam for transmission having the wavelength of 1300 nm, a collimating lens 40, a half mirror 41, a band pass filter for transmitting communication light which has the wavelength of 1300 nm, a condenser lens 43, and a detecting device 44 for receiving light.

The control system of the control box 2 operated as follows. Namely, a signal from an operation device 45, having operation switches, is sent to a microcomputer 47 directly or through an A/D converter 46. On the other hand, the amount of the light detected by the light detecting device 34 is inputted to an input monitor circuit 48 and further to the microcomputer 47 through the A/D converter 46. Therefore, the microcomputer 47 communicates the output information of the emitting power of the argon treatment laser 3 to the apparatus body by commanding the transmitting communication laser 39 to emit through a transmitting laser driving device 50. Further, after receiving the signal from a trigger switch 51, the microcomputer 47 transmits a signal into the apparatus body 1 in order to insert a filter 52, into the observing optical path to protect the eye of an oculist, and to move a attenuator 5 outside of the optical path.

As mentioned above, in the control box 2, communication light is transmitted from the control box 2 through the optical fiber 8 into the apparatus body 1 by the emission of the transmitting semiconductor laser 39 through the laser transmitting drive device 50, and the communication light, received from the apparatus body 1 through the optical fiber in the control box 2, is detected by the light detecting device 44 for processing in the signal processing circuit 53. Since communication light and treatment light are commonly carried by the optical fiber 8, control box movement is facilitated without cable entanglement problems of the prior art.

FIG. 2 shows a block diagram to show the arrangement of the apparatus body and an adaptor in a second embodiment of the present invention.

Apparatus Body For Photocoagulation

In the apparatus body, a semiconductor 60 for emitting the treatment light having a wavelength of 800 nm consists of two light sources combined with optical members (not shown). The light beam emitted from the semiconductor 60 is formed of a parallel luminous flux through a collimating lens 61. Although not shown it is preferable to remove the astigmatism by a cylindrical lens. A part of the light beam is reflected on a beam splitter 62 to input into a light detecting device 64 through a condenser lens 63.

Numeral 65 is a shutter for opening or closing the optical path of the semiconductor laser beam. A dichroic mirror 66 transmits the treatment light beam of 800 nm emitted from the semiconductor laser 60 and reflects the communication light of 1300 nm. And then, a dichroic mirror 67 transmits the light beam of a wavelength of more than 800 nm, while reflecting that of 630–670 nm. The beam transmitted through the dichroic mirror 67 is condensed into an optical fiber 71 through a condensing lens 70.

The aiming light beam emitted from an aiming light emitting laser 68, after formed into a parallel luminous flux by a collimating lens 69, is coaxial with the treatment light by the dichroic mirror 67.

The reflected light beam on the dichroic mirror 66, transmitted from the adaptor through the optical fiber 71, is introduced into a light detecting device 77 through a half mirror 74, a band pass filter for transmitting the light beam of wavelength of 1300 nm, and a condensing lens 76.

The transmitting light beam having a wavelength of 1300 nm emitted from a semiconductor laser 72 is formed into a parallel luminous flux by a collimating lens 73, and after being reflected on a half mirror 74 and the dichroic mirror 66, the transmitting light beam is condensed into the optical fiber 71 through the dichroic mirror 67 and the condensing lens 70.

The control system in the apparatus body is not explained here because it is approximately the same as that of the first embodiment, except that the aiming light beam is obtained by employing a visible laser instead of an attenuator.

Adaptor

The emitted light from the optical fiber 71 is formed into a parallel luminous flux by a collimating lens 80, and while its wavelength of 630–670 nm, 800 nm are transmitted through a dichroic mirror 81, its wavelength of 1300 nm is reflected thereon. Therefore, the optical path for communication light is shared with the optical path for the treatment light by including the dichroic mirror 81 respectively.

The communication optical system in the adaptor comprises a semiconductor laser 82 applying a wavelength of 1300 nm, a collimating lens 83, a half mirror 84, a band pass filter 85 which transmits the light having a wavelength of 1300 nm, a collimating lens 86, and a light detecting device 87.

The input monitoring optical system consists of a beam splitter 88 which reflects a part of the laser beam, a collimating lens 89, and a light detecting device 90.

A filter 91 cuts the communication light emitted from the semiconductor laser 72, which the light has a wavelength of 1300 nm. Further, the treatment light beam of 800 nm is emitted from a semiconductor laser 92, and formed into a parallel luminous flux by a collimating lens 93. The optical path of the treatment light is opened or closed by a shutter 97. An optical system to detect the emitting power of the semiconductor laser 92 consists of a beam splitter 94, a condensing lens 95 and a light detecting device 96.

A mirror 98 has partly different specific characters, that is, its center part reflects the laser beam emitted from the apparatus body, and its other part transmits the light from the semiconductor laser 92. Therefore, although it is not clear in FIG. 2, the optical path of the semiconductor laser 92 is not coaxial with the optical path of the laser from the apparatus body. After that, both laser beams become coaxial by input into a fiber 100 through a condensing lens 99. For details, reference is made to Japanese Patent application No. HEI 2-312006.

Next, the control system in the adaptor operates as follows. Namely, based on the control signal of an operation device 101, a microcomputer 102 controls the semiconductor laser 82 through a transmitting laser driving device 103 in order to send the transmitting signal to the apparatus body, while commanding a laser driving circuit 105 of a semiconductor laser 92 through a D/A converter 104 to emit the treatment light.

Based on the detected signal of the light detecting device 90, an input monitor circuit 106 monitors the emitting power of the emitted light from the optical fiber 71, and sends the monitored signal into the microcomputer 102 through an A/D converter. Therefore, the microcomputer 102 commands the apparatus body to increase the emitting power if that of the optical fiber 71 is not sufficient, further, to close the shutter 65 and the operation device 101 to display if the abnormal emission of the laser beam is detected. The emitting power of the semiconductor laser 92 is monitored at a monitor circuit 107.

Further, after receiving a signal from a trigger switch 108, the microcomputer 102 controls a filter 110 for protecting the eye of an oculist 110, and opens the shutter 65, besides, the shutter 97 through the shutter drive circuit 109 if necessary.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for optical treatment using a light beam comprising an apparatus body and a light relaying device for introducing treatment light emitted from said apparatus body into a delivery unit, wherein the apparatus body is connected with the light relaying device through an optical transmission cable, said apparatus body further comprising: treatment light emitting means which emits the light for optical treatment; first communication light emitting means which emits communication light for transmission to said light relaying device through said optical transmission cable; first communication light receiving means which receives communication light transmitted to said apparatus body through said optical transmission cable; and first control means which controls the treatment light emitted from said treatment light emitting means and the communication light emitted from said first communication light emitting means, and further generates a first received communication signal from the communication light received by said first communication light receiving means; and said light relaying device comprising: light separating means which separates the treatment light and the communication light emitted from said apparatus body and transmitted through said optical transmission cable; second communication light receiving means which receives the communication light separated by said light separating means; second communication light emitting means which emits communication light for transmittal to said apparatus body through said optical transmission cable; second control means which controls the treatment light emitted from said treatment light emitting means and the communication light emitted from said second communication light emitting means, and further generates a second received communication signal from the communication light received by said second communication light receiving means.

2. An apparatus for optical treatment using a light beam according to claim 1 wherein said optical transmission cable consists of an optical fiber cable.

3. An apparatus for optical treatment using a light beam according to claim 1, wherein said treatment light emitting means and the first communication light emitting means arranged in said apparatus body, and the second communication light emitting means arranged in said relaying device consist of respective semiconductor laser beam oscillators, at least the treatment light emitted from said treatment light emitting means and the communication light emitted from said first communication light emitting means have different wavelengths.

4. An apparatus for optical treatment using a light beam according to claim 3, wherein the wavelength of the communication light emitted from the first communication light emitting means arranged in said apparatus body is the same wavelength as that of the communication light emitted from the second communication light emitting means which is arranged in said light relaying device.

5. An apparatus for optical treatment using a light beam according to claim 1, wherein the light separating means arranged in said light relaying device consists of a dichroic mirror which transmits the treatment light and reflects the communication light.

6. An apparatus for optical treatment using a light beam according to claim 1, wherein said apparatus body further comprises splitting means which applies a portion of the treatment light to a first monitor means for monitoring emitting power of the treatment light emitted from said treatment light emitting means.

7. An apparatus for optical treatment using a light beam according to claim 1, wherein said light relaying device further comprises a second monitor means monitoring the emitting power of the treatment light transmitted through said optical transmitting cable.

8. An apparatus for optical treatment using a light beam according to claim 7, wherein said light relaying device is provided with another treatment light emitting means for compensating emitting power of the treatment light emitted from the treatment light emitting means in said apparatus body, second control means for controlling the other treatment light emitted from said second treatment light emitting means based on a monitor signal transmitted from said second monitor means.

9. An apparatus for optical treatment using a light beam according to claim 8, wherein said second treatment light emitting means arranged in said light relaying device consists of a semiconductor laser beam oscillator which emits a light beam having the same wavelength as the treatment light emitting means arranged in the apparatus body.

10. An apparatus for optical treatment using a light beam comprising an apparatus body and a light relaying device which introduces a treatment light emitted from said apparatus body into a delivery unit by being connected with the apparatus body through an optical fiber cable, wherein said apparatus body comprises: a treatment laser beam oscillator for emitting treatment light; a first transmitting laser beam oscillator for emitting communication light to said light relaying device; a first receiving device for receiving the communication light to be sent from said light relaying device through said optical fiber cable; a first operation means for operating emitting power of the treatment light emitted from said treatment laser beam oscillator and that of the communication light emitted from the first transmitting laser beam oscillator; and a first control means which controls the emitting power of the treatment light emitted from said treatment laser beam oscillator and the communication light emitted from the first transmitting laser beam oscillator, and generates a received communication signal from the communication light received by said first receiving device; and said light relaying device comprising: a second receiving device for receiving the communication light emitted from the first transmitting laser beam oscillator in said apparatus body; a second transmitting laser beam oscillator for emitting the communication light into said apparatus body; a second operation means for operating a second transmitting laser beam oscillator to generate communication light; and a second control means which controls the communication light emitted from the second transmitting laser beam oscillator and generates another received communication signal from the communication light received by said second receiving device.

11. An apparatus for optical treatment using a light beam, which includes an apparatus body having a first control operation means for providing an optical treatment light and an optical fiber cable for transmitting the optical treatment light from said apparatus body into a delivery unit, comprising:

a light relaying device connected with both of said apparatus body and said delivery unit through the optical fiber cable;

second control operation means provided in said light relaying device;

respective optical communication means for transmitting and receiving communication light signals, said optical communication transmitting means and said optical communication receiving means being arranged in the light relaying device and said apparatus body respectively; and an optical system for introducing the communication light signals from said optical communication means into said optical fiber cable.

12. An apparatus for optical treatment according to claim 11, wherein the optical treatment light is a semiconductor laser beam, and a semiconductor laser is arranged in said light relaying device to compensate an emitting power of the optical treatment light.

13. An apparatus for optical treatment according to claim 11, wherein said optical system is provided with a filter for removing any treatment light from application to light detecting means which detects said communication light signals.

14. An apparatus for optical treatment according to claim 13, wherein said filter is a band pass filter.

15. An apparatus for optical treatment according to claim 11, wherein said treatment light is a laser beam for photocoagulation of an eye of a patient.

* * * * *